(12) United States Patent
Hayes et al.

(10) Patent No.: US 9,808,203 B2
(45) Date of Patent: Nov. 7, 2017

(54) METHOD FOR MOTION CORRECTION OF EMISSION COMPUTED TOMOGRAPHY DATA BY WAY OF MAGNETIC RESONANCE TOMOGRAPHY DATA

(71) Applicants: Siemens Aktiengesellschaft, Munich (DE); Universität Münster, Muenster (DE)

(72) Inventors: Carmel Hayes, Munich (DE); Ralf Ladebeck, Erlangen (DE); Klaus Schäfers, Telgte (DE)

(73) Assignees: Siemens Aktiengesellschaft, Munich (DE); Westfaelische Wilhems-Universitaet Muenster, Muenster (DE)

( * ) Notice: Subject to any disclaimer, the term of this patent is extended or adjusted under 35 U.S.C. 154(b) by 686 days.

(21) Appl. No.: 14/282,282

(22) Filed: May 20, 2014

(65) Prior Publication Data
US 2014/0357980 A1    Dec. 4, 2014

(30) Foreign Application Priority Data
May 28, 2013    (DE) .................. 10 2013 209 939

(51) Int. Cl.
*A61B 5/00*    (2006.01)
*A61B 5/055*    (2006.01)
(Continued)

(52) U.S. Cl.
CPC .......... *A61B 5/7207* (2013.01); *A61B 5/0035* (2013.01); *A61B 5/0044* (2013.01);
(Continued)

(58) Field of Classification Search
CPC ....... A61B 5/721; A61B 5/055; A61B 5/0035; A61B 6/5264; A61B 6/037; A61B 6/5205;
(Continued)

(56) References Cited

U.S. PATENT DOCUMENTS

| 2006/0184002 A1* | 8/2006 | Yarnykh | ............ | G01R 33/5607 |
| | | | | 600/410 |
| 2006/0266947 A1 | 11/2006 | Krieg et al. | | |
| 2012/0068704 A1* | 3/2012 | Popescu | ............ | G01R 33/5611 |
| | | | | 324/309 |

FOREIGN PATENT DOCUMENTS

DE    102005023907 A1    12/2006

OTHER PUBLICATIONS

Ouyang et al., "Magnetic Resonance-Based Motion Correction for Positron Emission Tomography Imaging," Semin Nucl Med, vol. 43, No. 1, Jan. 2013, pp. 60-67, available online: Nov. 22, 2012.*
(Continued)

*Primary Examiner* — Elmer Chao
(74) *Attorney, Agent, or Firm* — Harness, Dickey & Pierce P.L.C.

(57) ABSTRACT

A method includes introducing the examination object into an examination region of a combination device; recording emission computed tomography data over a measurement period and storing detection events and detection instants associated therewith; measuring magnetic resonance data of at least two subregions of the examination region at at least two instants during the recording period of the emission computed tomography data and storing the magnetic resonance data and the recording instants; determining motion information describing a motion of a region of the examination object at a first instant relative to the position at a second instant from the magnetic resonance data recorded at the first instant and the second instant, for each subregion;
(Continued)

determining a motion model describing motion of the examination object, for the entire object, from information for the subregions; and calculating motion-corrected emission tomography data from detection events, detection instants and the motion model.

15 Claims, 4 Drawing Sheets

(51) Int. Cl.
| | |
|---|---|
| A61B 6/00 | (2006.01) |
| A61B 6/03 | (2006.01) |
| G06T 7/00 | (2017.01) |
| G01R 33/48 | (2006.01) |
| G01R 33/565 | (2006.01) |
| G01R 35/00 | (2006.01) |

(52) U.S. Cl.
CPC ............ *A61B 5/055* (2013.01); *A61B 5/742* (2013.01); *A61B 6/037* (2013.01); *A61B 6/4417* (2013.01); *A61B 6/503* (2013.01); *A61B 6/5264* (2013.01); *A61B 6/5247* (2013.01); *A61B 2576/023* (2013.01)

(58) Field of Classification Search
CPC ... A61B 6/4417; A61B 6/5247; G06T 7/0024; G06T 2207/10016; G06T 2207/10088; G06T 2207/10104; G01R 33/481; G01R 33/56509

See application file for complete search history.

(56) References Cited

OTHER PUBLICATIONS

Gigengack, F. et al: "Mass-preserving motion correction of PET: Displacement field vs. spline transformation." Nuclear Science Symposium and Medical Imaging Conference (NSS/MIC), 2011 IEEE, pp. 3088-3090, 2011).; 2011.
McQuaid, Sarah: Characterisation and Correction of Respiratory-Motion Artefacts in Carciac PET-CT; http://eprints.ucl.ac.uk/19732/; 2009.
Büther, F. et al: List-mode driven cardiac and respiratory gating in PET. Journal of nuclear medicine; official publication, Society of Nuclear Medicine 2009;50: 674-681; 2009.
Le Meunier, Ludovic: Motion frozen 18F-FDG cardiac PET; Journal of Nuclear Cardiology, Apr. 2011; 18 (pp. 259-266); 2011.
Pys. Med. Biol. 56 (2011) 6597-6613 "Fast generation 4D PET-MR data from real dynamic MC acquisitions".
Würslin C. et al; "Respiratory Motion Correction in Oncologlc PET Using T1-Weighted MR Imaging on a Simultaneous Whole-Body PET/MR System"; The Journal of Nuclear Medicine; vol. 54; No. 3; pp. 464-471; ISSN: 2159-662X; 2013.
German Office Action Application No. 10 2013 209 939.8 dated Jan. 30, 2014.

* cited by examiner

METHOD FOR MOTION CORRECTION OF EMISSION COMPUTED TOMOGRAPHY DATA BY WAY OF MAGNETIC RESONANCE TOMOGRAPHY DATA

PRIORITY STATEMENT

The present application hereby claims priority under 35 U.S.C. §119 to German patent application number DE 102013209939.8 filed May 28, 2013, the entire contents of which are hereby incorporated herein by reference.

FIELD

At least one embodiment of the invention generally relates to a method for motion correction of emission computed tomography data in a combination device for magnetic resonance tomography and emission computed tomography.

BACKGROUND

Emission computed tomography measurements, in particular positron emission tomography (PET), are valuable methods in particular for obtaining information about metabolic, pharmacological or molecular processes. Since in an emission computed tomography procedure high doses of radiation are to be avoided, narrow limits are set for a maximum radiation dose to be used. Hence measurements using emission computed tomography procedures regularly require measuring times lasting several minutes. If moving objects are examined, with motion of the internal organs being unavoidable particularly when examining living beings, only blurred measurements can be achieved in this way.

A known remedy for this is to correct the motions. Thus it is for example possible to estimate motion data from PET data, in which for example the center of mass of the radiating region is tracked. Alternatively, gating methods are used, i.e. methods in which only detection events of a particular motion phase are used. Gating is possible for example by recording an electrocardiogram during the emission computed tomography measurement and sorting the data on the basis of the cardiac cycle. Besides using data from just one phase, it is also possible to use data from several phases thanks to a motion correction. It should be noted here however that a motion correction from emission tomography data alone is made more difficult by the noisy signal.

Methods are also known in which emission tomography data is corrected using computed tomography data from a trans-irradiating method. This has the advantage that information about the attenuation of the radiation by the tissue can be determined simultaneously using relatively high-contrast images from the computed tomograph systems. However, if a periodic or pseudoperiodic motion of an internal organ is to be corrected, several recordings must be made for each motion cycle. This results in a considerable increase in exposure to radiation.

From C. Tsoumpas et al., Phys. Med. Biol. 56 (2011) 6597-6613, the entire contents of which are hereby incorporated herein by reference, it is known that when using combined PET-MR data, a motion correction of the PET data is also possible using the magnetic resonance data. While the publication exclusively works with simulated PET data, it shows that a motion correction of emission computed tomography data using magnetic resonance data is at least possible. In this case, although the MR measuring time is reduced by optimizing the measurement protocol and adjusting the resolution, only a temporal resolution of 0.7 seconds is achieved. If it is desired to correct faster motions, such as a motion of the heart on the basis of the pulse for example, this temporal resolution is not sufficient. To be able to map a motion at all reliably, more than two images per motion cycle should be recorded. To identify a more precise form of motion or asymmetries of motion, even higher temporal resolutions are required. Simply reducing the measurement resolution may indeed cut the measuring time, but the spatial resolution then deteriorates.

SUMMARY

At least one embodiment of the invention specifies a method for motion correction.

At least one embodiment of the method, comprises:
Introduction of the examination object into an examination region of the combination device,
Recording emission computed tomography data over a measurement period and storage of detection events and detection instants associated therewith,
Measurement of magnetic resonance data of at least two subregions of the examination region at at least two instants during the recording period of the emission computed tomography data and storage of the magnetic resonance data and of the recording instants,
Determination of at least one item of motion information which describes a motion of a region of the examination object at a first instant relative to the position at a second instant from the magnetic resonance data recorded at the first instant and the second instant, for each subregion,
Determination of a motion model which describes the motion of the examination object, for the entire examination object, from the motion information for the subregions,
Calculation of the motion-corrected emission tomography data from the detection events, the detection instants and the motion model.

At least one embodiment of the present invention further relates to a combined emission tomography and magnetic resonance tomography device, wherein it is designed to carry out at least one embodiment of the method.

BRIEF DESCRIPTION OF THE DRAWINGS

The further advantages and details of the invention will emerge from the following example embodiments and drawings, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the method, comprises:
Introduction of the examination object into an examination region of the combination device,
Recording emission computed tomography data over a measurement period and storage of detection events and detection instants associated therewith,
Measurement of magnetic resonance data of at least two subregions of the examination region at at least two instants during the recording period of the emission computed tomography data and storage of the magnetic resonance data and of the recording instants,
Determination of at least one item of motion information which describes a motion of a region of the examination object at a first instant relative to the position at a second instant from the magnetic resonance data recorded at the first instant and the second instant, for each subregion,
Determination of a motion model which describes the motion of the examination object, for the entire examination object, from the motion information for the subregions,
Calculation of the motion-corrected emission tomography data from the detection events, the detection instants and the motion model.

At least one embodiment of the invention is based on the idea that for precise motion correction it is not necessary to detect the motion in the entire space, but that it is sufficient to determine the motions at a few selected positions. Motions of the tissue at intermediate positions can then be calculated with the aid of a model which can for example be determined from the data from a high-resolution magnetic resonance tomography recording of the entire examination region and/or a plurality of previously recorded images of comparable examination objects. Compared to a general reduction in the resolution, the advantage of this approach is that in the regions in which motion is of particular relevance imaging can take place with a high temporal resolution, while less relevant regions are not mapped at all. This means that overall a data set providing high-resolution motion information about an examination object can be measured in very short spaces of time. Thus for example using a high repetition frequency solely the image region in which the heart is situated can be mapped and using a somewhat lower repetition rate an image region providing information about the motion of a diaphragm can be mapped.

Thus two or more smaller regions can be mapped, possibly using a different repetition rate. The mappings of these regions provide motion information that can be transferred to a model present in the memory of an evaluation device. Using this model a close approximation of the overall motion of the tissue can be determined, even in regions not recorded by the MR data. Thus an overall motion is determined from a plurality of motion information determined from a single region in each case, and from a previously established motion model. Thus it is possible to calculate a temporally and spatially high-resolution motion.

The motion model parameterized by the motion information determined therefore takes the place of the 4D data set known from the publication by Tsoumpas et al. The motion model therefore represents motion data for every point in the three-dimensional space recorded using the PET scanner. Motion-corrected PET data can be calculated from the motion information for every point in the three-dimensional space and the detection instants of the detection events. In the simplest case this can take place by means of simple gating, in other words the selection of data belonging to the same motion phase. As long as the overall motion recurs cyclically, it is therefore possible to compute an overall image from a subset of the PET data. However, even in this simple case gating using MR data has advantages compared to gating using external triggering or gating solely based on the PET data. Gating in the inventive method depends solely on an actual motion, and so a motion path is measured directly rather than being derived from further data. Greater reliability and precision are achieved compared to gating based on PET data or using data from further measurement devices, such as a respiratory belt for example.

To achieve a better contrast, a reconstruct transform average (RTA) approach is normally followed as the simplest method of motion-corrected PET data reconstruction. Normally a motion cycle is divided into several phases by an external gate signal, or one determined from the PET data. A reconstruction image is first calculated separately for each of these phases. In the normal methods a transformation between the individual phases is then calculated from PET data. Then all phases are transformed so that they correspond to a common motion phase and the overall image is calculated by averaging the different motion-corrected phases. However, one problem with this is the high susceptibility to interference of the PET data and the frequently low contrast. This therefore makes it more difficult to reliably calculate a transformation. The inventive method has significant advantages here, as to calculate the back-transformation use is made of the MR data or the motion model calculated therefrom. High-resolution, low-noise data is therefore available for the transformation calculation between the PET data of different motion phases. Thus the quality of the reconstruction can be improved and artifacts prevented.

Alternatively, in motion-compensated image reconstruction (MCIR) the motion compensation is integrated into the image reconstruction. Here too, the presence of an overall motion model which specifies a motion of the tissue for every point in the three-dimensional space has great advantages. If motion data is determined solely from PET data, tissue regions that have not absorbed any contrast agent cannot be identified. Thus nor can the motion of these parts of the tissue be used to compute motion fields. MR data in particular maps the water content in the tissue. In this way the entire tissue can be mapped with high contrast. Better output data is therefore available in order to calculate motion fields for the individual points in space.

The use of the motion fields for reconstruction is to be explained here using the simple example of backprojection. Similarly, the motion data can also be used in iterative reconstruction methods. These methods are known in the prior art and require no further explanation here. To understand the principle of reconstruction, an explanation using backprojection by way of example is however sufficient. With PET data a line on which the dematerialization of a positron and an electron into two protons takes place is determined unambiguously. With backprojection, the value of all voxels (i.e. three-dimensional pixels) lying on this line is thereby increased by a certain amount. When all measured decay events are overlaid, an image is created. The image quality can be improved still further by filtering. Since a motion relative to a starting position is known from the motion model for each point in space, the values of the points displaced according to the motion pattern compared to the straight line of coincidence can be increased. Thus overall a motion-corrected image is computed.

It is particularly advantageous, in at least one embodiment of the inventive method, if the magnetic resonance data is recorded one- or two-dimensionally for at least one of the subregions. In the simplest case data is recorded in MR tomography recordings such that one plane of the mapping region is excited, a phase shift in a further direction is created by a gradient field and a magnetic field gradient which during recording shifts the frequencies of the nuclear spins compared to one another is overlaid in a third direction. Thus in order to map a three-dimensional region, as many recordings are required in this case as the product of the number of points in two directions of the image.

In order for example to record a two-dimensional plane, excitation may take place in just one plane. The further excitations of the adjacent planes in order to obtain a three-dimensional image are not necessary. Only in this way can the recording speed be increased by several orders of magnitude. Two-dimensional measurements using the MR tomography system are, depending on the measurement protocol, typically possible in approximately 10 ms.

For certain regions an excitation with a 2D high-frequency pulse can also take place. In this case only nuclear spins along a straight line are excited. Therefore no further phase coding is necessary, and a gradient field need only be overlaid in the direction of the straight line in order to achieve a shift in the resonance frequency along this straight line. Thus only a high-frequency pulse and the read-out while a gradient field is applied in one direction is necessary. A measurement of this type can take place in approximately one ms.

Thus, motion information can be recorded very fast if for example two or three planes lying perpendicular to one another are placed through an object of interest and an MR measurement takes place for each of these planes. For even faster data recording, it may sometimes also be advantageous to measure only lines of intersection through objects. Thus for example nine planes of intersection and ten lines of intersection can be measured in the region of interest and the measurement may furthermore be faster than 100 ms, which means that it is still possible to resolve the heartbeat into several phases.

To record a one-dimensional magnetic resonance data set use can be made of a two-dimensional high-frequency pulse.

In many cases the overall motion inside an examination object comprises several motions that occur on different timescales. To achieve an optimum measurement of the motions it is hence advantageous if the time interval between two recordings of magnetic resonance data for the first subregion differs from the time interval between two recordings of magnetic resonance data for at least a second of the subregions. Thus for example motions in a region in which very fast motions are expected can be determined by measuring a few lines of measurement in this region. Thus it is possible to determine the motion information in a few ms. For regions that move slowly, two-dimensional or even three-dimensional recordings in a limited region are however possible. If the recording for different regions takes place consecutively, it may be advantageous for the measurement protocol for measurements at regions that take place at longer time intervals to be interrupted by faster measurements for other regions. It is of course also possible to set the whole examination region as one of the regions. In this case an MR data set can be recorded with a lower sampling rate, i.e. at an interval of several seconds, and can be used for example to correct the motion of the entire body. At the same time regions in which a very fast motion is expected can be measured at a measurement interval of a few or a few tens of ms.

Additionally or alternatively it is also possible for the resolutions of the magnetic resonance measurements in at least two of the subregions to be different. A high measurement resolution is frequently necessary in some of the regions recorded to predict the overall motion in a motion model, but in other regions it is sufficient to use lower resolutions to obtain information about the motion. Because the individual regions are recorded independently of one another, different resolutions can be used in this case for different regions. Moreover it is also possible to adjust the resolutions in different spatial directions independently of one another. Thus for example in one region it is possible to measure at high resolution in a first direction and at low resolution in a second direction, while in a further region the measurement in the first direction is at a low resolution and in the other two spatial directions it is at a higher resolution. By measuring MR data independently in several measurement regions a weighting between spatial and temporal resolution is thus possible for each measurement region individually.

It is possible for the magnetic resonance measurements of at least two of the subregions to take place at different instants. In this case each of the measurements takes place completely independently, i.e. the measurements are carried out as if they were individual measurements. Alternatively at least the excitation of at least two subvolumes for the magnetic resonance measurement can take place simultaneously.

If the excitation of the at least two subvolumes takes place simultaneously it is possible for a simultaneous magnetic resonance measurement for at least two subregions to take place by using at least two local coils. If two regions, spaced apart from one another, of an examination object are to be recorded, it is thus possible to record measurement values from two regions simultaneously. In this case the region situated closer to the local coil couples into the local coil much more strongly than the more remote one. Thus parts of the measurements can take place in parallel.

Moreover simultaneous magnetic resonance measurements for at least two subregions can take place by overlaying a second readout gradient. When overlaying two readout gradients, a summation of the magnetic fields occurs initially. Thus initially only one rotation of the measurement region takes place. However, it is now for example possible to apply a relatively weak field in one spatial direction, the sole purpose of which is to mistune the resonances slightly in respect of one another and thus to enable the positions along this spatial direction to be differentiated. A strong field can be applied in the other spatial direction. Because of the finite expansion of the measurement region the weak field only results in a splitting of the frequencies within a relatively narrow frequency band. If the two measurement regions are sufficiently far apart from one another and the second field applied is strong enough, this means that the frequency split of the resonance frequencies of the nuclear spins between the regions is so large that the bands read out for the regions can nevertheless be differentiated and do not overlap one another.

To permit a resolution of fast motions of individual parts of the examination object it is advantageous if the time interval between two measurements of at least one subregion is between 1 and 100 ms, in particular between 1 and 40 ms. In the region of 1 ms or also somewhat less, one-dimensional measurements of regions are possible. Measurements of a two-dimensional region are possible in approx. 10 ms. If the measurements are made consecutively, account should be taken when calculating the shortest possible time interval of the fact that at least parts of other measurements are to take place in this time interval. However, a high-frequency measurement is often necessary only for a small number of measurement regions in which it is sufficient to measure one- or two-dimensionally. Other measurement regions can be measured such that the measurement of these regions to be measured more slowly is interrupted numerous times by faster measurements of the regions to be measured at high frequency.

It is particularly advantageous if the emission computed tomography is PET tomography. PET tomography has many advantages, particularly because of the fact that a measurement event can be validated by a coincidence and that a clear line on which the event to be resolved is to be located is specified by the two coincidences.

At least one embodiment of the inventive method permits movement correction of emission tomography data which has a particularly high temporal resolution. Hence it is very suitable for use for fast motions in an examination object, in particular for correction of the motion of the heart caused by cardiac contraction.

At least one embodiment of the present invention further relates to a combined emission tomography and magnetic resonance tomography device, wherein it is designed to carry out at least one embodiment of the method.

Figure 1:
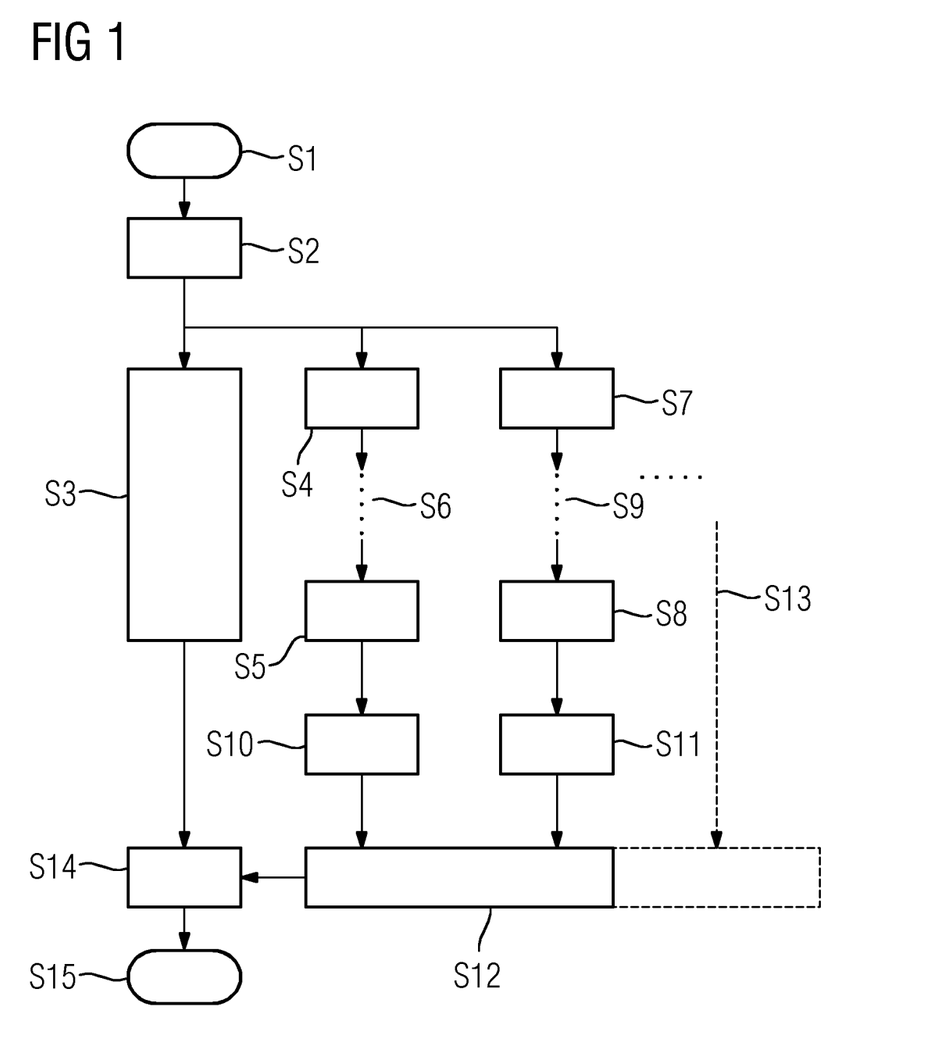
FIG. 1 shows a schematic flow chart of an embodiment of the inventive method.

FIG. 1 schematically shows a sequence of a method for motion correction of emission computed tomography data in a combination device for magnetic resonance tomography and emission computed tomography. After the start of the method S1 the examination object is introduced into an examination region of the combination device in step S2. It is here possible, in particular in the emission computed tomograph system, for only parts of the examination object to be mapped. In this case a first region of the examination object is introduced into the examination region and then the examination object is moved piece by piece through the examination region by means of an automatic traversing unit.

After introducing the examination object into the examination region, emission computed tomography of the examination object is recorded in step S3. In emission computed tomography decay events of a contrast agent are registered in the examination object and are stored with the location and time of their detection. Recording emission tomography normally takes several minutes. Hence if parts of the examination object move, any motion results in blurring. This is to be prevented or corrected here.

To achieve this at least four magnetic resonance tomography measurements are carried out in this method. The magnetic resonance tomography measurements take place at at least two different regions. Thus a first magnetic resonance tomography data set is recorded for a first region in a first step S4 and a second magnetic resonance tomography data set for the same region is recorded, separated by time, in step S5. The dotted region in the diagram S6 shows that besides the two recordings in steps S4 and S5, still further magnetic resonance recordings of the same region can be carried out. For a second region in step S7 a first and in step S8 a second magnetic resonance tomography is likewise recorded. Here too, as indicated with the dotted region S9, several further measurements can be carried out, separated by time. Immediately as indicated by the dotted region S13 further examinations can be carried out in parallel at further regions.

It should be noted here that the regions recorded can be recorded in as many different ways as desired. Thus for example in S4 and S5 a high-resolution three-dimensional magnetic resonance tomography can be recorded, with each measurement lasting 30 seconds, whereas the region recorded in S7 and S8 is recorded one-dimensionally and is recorded within a ms. However, similar regions can also be recorded, for example a plane of intersection through a heart can be recorded in S4 and S5 and a further plane of intersection through a heart in S7 and S8. The type and number of the regions to be recorded can be freely selected here. It is important that several one-, two- or three-dimensional regions are recorded independently of one another, and that at least two different recordings separated by time are made for each of these regions.

Generally several recordings are made for each region, with the time interval between the recordings for one region possibly differing from the time interval between the recordings for another region. On completion of the measurement first motion information is obtained in step S10 from the magnetic resonance tomographies for the first region which were taken in steps S4 and S5 and potentially in the further steps S6. This first motion information may for example be one-dimensional motion information. The first motion information may however also involve a plurality of individual data items which for example describe a two-dimensional deformation of a line or a displacement of several objects. Likewise in step S11 further motion information is determined from the further magnetic resonance tomographies recorded in step S7 and S8 and potentially in step S9. Further motion information can also be determined from the further regions indicated in region S13, in which magnetic resonance tomographies were created. It should be noted here that the calculation of the motion information, even though it is represented here as a final step following conclusion of the emission computed tomography measurement in step S3, can of course take place wholly or partially during the emission computed tomography measurement.

A motion model is calculated in step S12. The calculation of the motion model uses the motion information calculated in step S10 and step S11, as well as any motion information intended for further regions. A motion model is an instruction for how the motion of the individual voxels, i.e. the three-dimensional points of the emission tomography data, can be calculated from the individual items of motion information for the regions. Models of this type can be created in a variety of ways. To create this type of model, a large number of measured 4D data sets for similar examination objects is evaluated for example.

To obtain information about rapid motions, combined data sets comprising transirradiation computed tomograph systems and MR computed tomograph systems can be used for example to determine the motion model. It is also possible to obtain the motion model from other correlated information, such as for example electrocardiograms, respiratory measurements, external video systems, etc. Motion models may be created either manually or by simulation and/or machine learning. It is also possible to calculate unknown regions simply by using B splines or similar interpolation methods. Thus normally a method which is a mixture of mathematical interpolation, comparison with a model formed from a plurality of previous measurements and consideration of general basic principles such as the retention of masses and elasticity of the tissue is used as a motion model.

The result of the calculation of the motion model in step S12 is essentially equivalent to a four-dimensional magnetic resonance data set. The resulting four-dimensional data set can either be stored explicitly in the memory, or the motion of the individual points can be parameterized by the model. It is important that a temporal motion sequence is determined for each of the voxels. This motion model is used in step S4 to correct the emission tomography data. Preferably an MCIR algorithm is used here, as by taking the motion into account right from the image reconstruction stage better results are frequently obtained. If the measurements are very noisy, it may however be advantageous to use an RTA algorithm which may be more stable in the face of interference. An iterative expectation maximization algorithm is generally used for the image reconstruction itself. These algorithms are based on the fact that a three-dimensional input data set is input into the method, an expected distribution of the emission tomography detector signals is calculated from this data set and in an iterative method the input data set is adjusted such that the deviation from the measured data is minimized. However, it is of course also possible to use filtered backprojection or other algorithms.

After the calculation of the corrected emission tomography data S14 the method concludes in step S15 and the calculated data can then be further processed or displayed.

Figure 2:
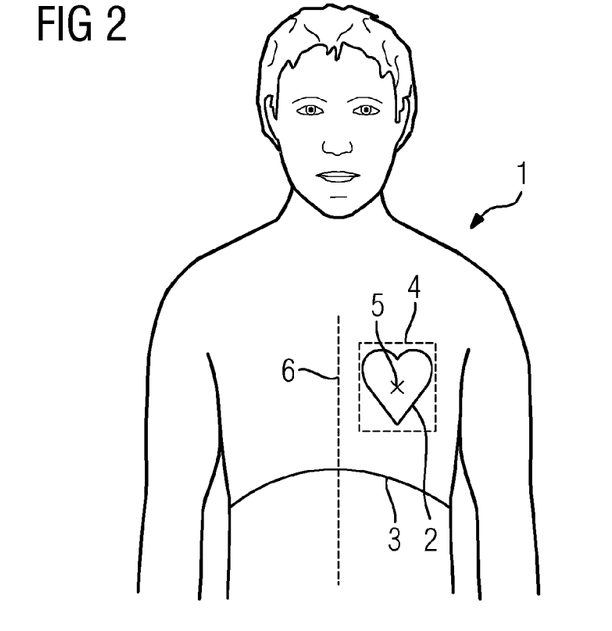
FIG. 2 shows a schematic representation of the measurement regions for motion correction of PET data for the heart.
Figure 3:
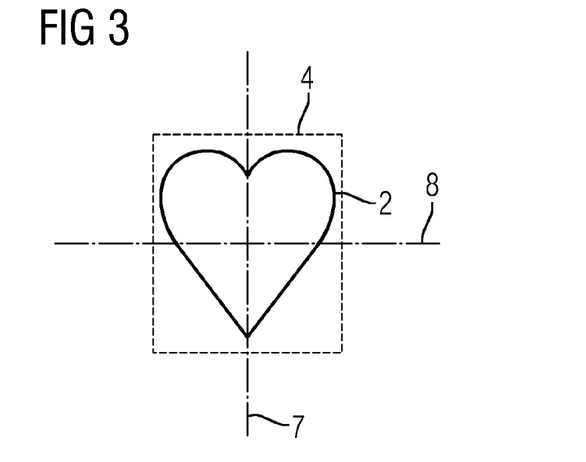
FIG. 3 shows a schematic representation of an alternative arrangement of the MR measurement regions for motion correction of a heart.
Figure 4:
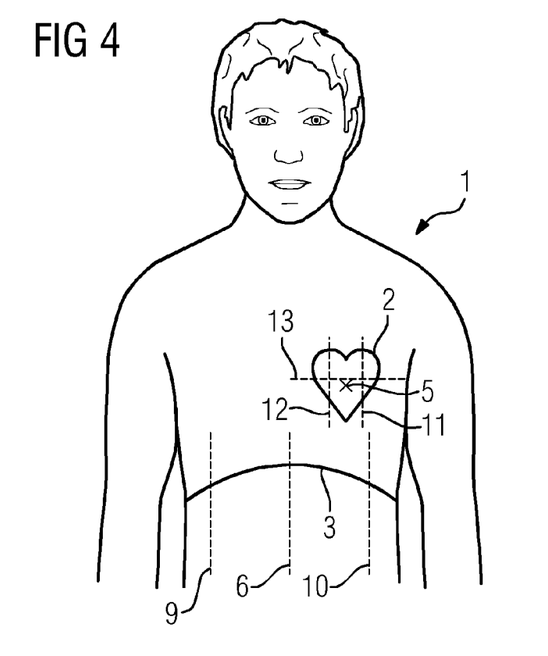
FIG. 4 shows a schematic representation of a third possible arrangement of the MR measurement regions for carrying out motion correction of the motion of a heart.

FIG. 2 to FIG. 4 show some examples of which regions can be used for motion detection, in order to compensate for the motion of the heart in an emission tomography method.

FIG. 2 shows a person as an examination object 1, the aim being to perform motion correction for PET tomography of the heart 2. The motion of the diaphragm 3 is also crucial for the motion of the heart 2, in addition to the beating of the heart. A motion correction should be carried out here by measuring three regions. Firstly a two-dimensional plane 4 running through the heart is measured, and additionally a one-dimensional region 5 lying perpendicular thereto and a region 6 lying perpendicular to the diaphragm 3 are measured.

The motion of the diaphragm 3 of the person 1 can readily be modeled. Additionally, before carrying out the PET examination, recordings of the examination object can be made to enable the model to be adjusted to the examination object. Thus it may be sufficient to measure an individual variable in order to determine the motion of the diaphragm in full. Hence in this exemplary embodiment only the one-dimensional region 6 is measured in order to detect the motion of the diaphragm 3. The diaphragm has a motion cycle corresponding to the respiratory frequency, i.e. region 6 need only be measured multiple times on a time scale of approx. 5 seconds. It is also fully sufficient to measure the region 6 with a temporal resolution of approx. 500 ms.

The motion of the heart 2 itself is determined within the image plane by a measurement of a two-dimensional MR data set 4. This type of two-dimensional data set can be recorded in approx. 10 ms. With a data set of this type displacements of the heart within this plane can firstly be established. This can additionally be used as a correction of the motion of the heart through respiration. Furthermore, the expansion and contraction of the heart in the plane can be observed.

Finally the measurement region 5 is likewise measured one-dimensionally perpendicular to this plane. This has several advantages. Firstly the measurement of the region 5 permits a very high-frequency measurement of the motion of the heart. Secondly a value for the height expansion of the heart is always specified in addition to the lateral expansion. Thus the motion of the heart can be better modeled.

It should further be noted that regardless of the type of examination object, it is possible for an overall motion to be calculated after recording just a few MR data sets per region, and that it is also possible for this calculated overall motion to be used to adjust the positioning and orientation of the measured regions. Thus for example by evaluating the measurement region 4, i.e. the position of the heart in the plane, the position of region 5 can be adjusted and vice versa.

FIG. 3 shows a further possible arrangement of the MR measurement regions for identifying the motion of the heart. Three two-dimensional MR measurements are used here. The region 4 runs through the plane of the heart in the image plane, as in FIG. 2. In addition, the planes 7 and 8 lying perpendicular to the region 4 are measured. In this way a two-dimensional motion of the heart is determined in three directions. This may be advantageous in particular for detailed deformation information. Measuring several planes in this way is possible with a repetition interval of 30-40 ms. In this way the motion of the heart can easily be divided into several phases, in order then to correct the motion.

FIG. 4 shows one possibility for the selection of measurement regions for particularly high-frequency measurements. Only one-dimensional measurement regions are used here. Three one-dimensional measurement regions 6, 9 and 10 are used here to measure the motion of the diaphragm. Four one-dimensional measurement regions 5, 11, 12 and 13 are laid through the heart 2. These measurement regions enable an overall motion to be readily estimated. The use of seven one-dimensional measurement regions allows the motion to be measured with a temporal resolution of less than 10 ms. If the temporal resolution of the measurement is to be increased still further, it is also possible to determine the motion data for the diaphragm from the regions 6, 9 and 10 less frequently and for this to increase the recording frequency of the measurement regions at the heart 2, i.e. the regions 5, 11, 12 and 13. Thus even measurements with a temporal resolution of less than 5 ms are possible. This corresponds to a measurement frequency of 200 Hz. A high measurement frequency such as this is generally not necessary in order to measure the heart or other bodily functions of humans or animals. Nevertheless, emission tomography measurements are imaginable on systems on which motions are to be determined with a very high frequency such as this.

Figure 5:
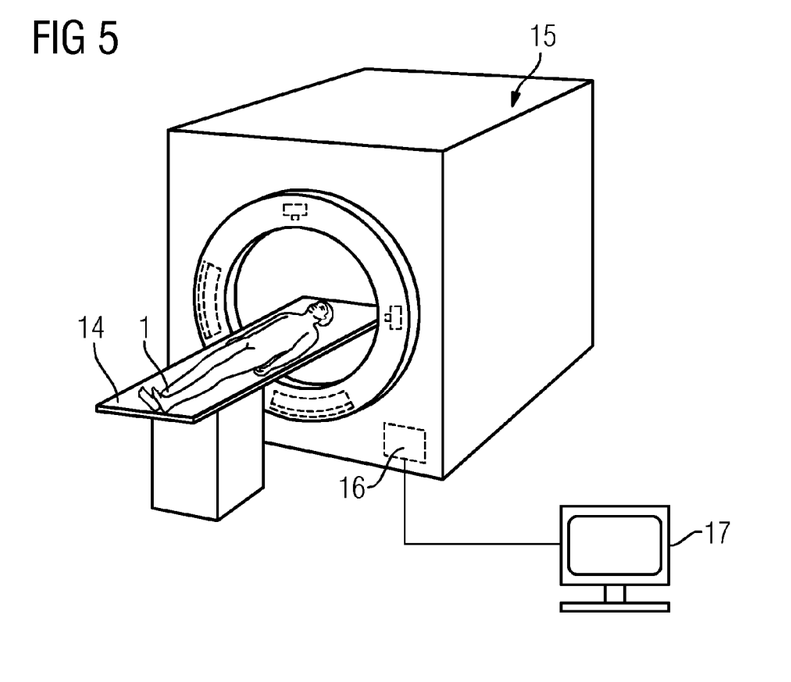
FIG. 5 shows an example embodiment of an inventive combined emission tomography and magnetic resonance tomography device.

FIG. 5 shows a schematic representation of an embodiment of an inventive combined emission computed tomography and magnetic resonance tomography device. The examination object 1 is in this case introduced on a support 14 into the combined emission computed tomography and resonance tomography device. A PET tomography system is used here as an emission tomography system. Besides the main magnetic field coils, gradient coils and local recording coils, the combined measuring device also comprises several parallel rings out of a plurality of scintillation detectors to detect the photons generated by positron electron annihilation.

The combined measuring device 15 comprises numerous connection facilities for local coils, which means it is possible to carry out magnetic resonance measurements at several measurement regions in parallel, which means the measurement frequency can be further increased. Furthermore, the combined measuring device 15 has an integrated control device 16. Whereas in principal all control and measuring tasks of a combined PET and MR measuring device 15 can be carried out by a computer 17, it is advantageous for a variety of reasons to use a control device 16 integrated into the combination device. This is firstly advantageous for safety reasons, to reliably enable a safe powering-down of the device, and secondly fast measurement sequences can thereby be used reliably and free from interference. The control device 16 is here designed to carry out several independent MR tomography measurements during a PET data recording. To this end the measurement regions can be selected on the control computer 17. This can be done fully automatically when selecting the motion model to be used.

Figure 6:
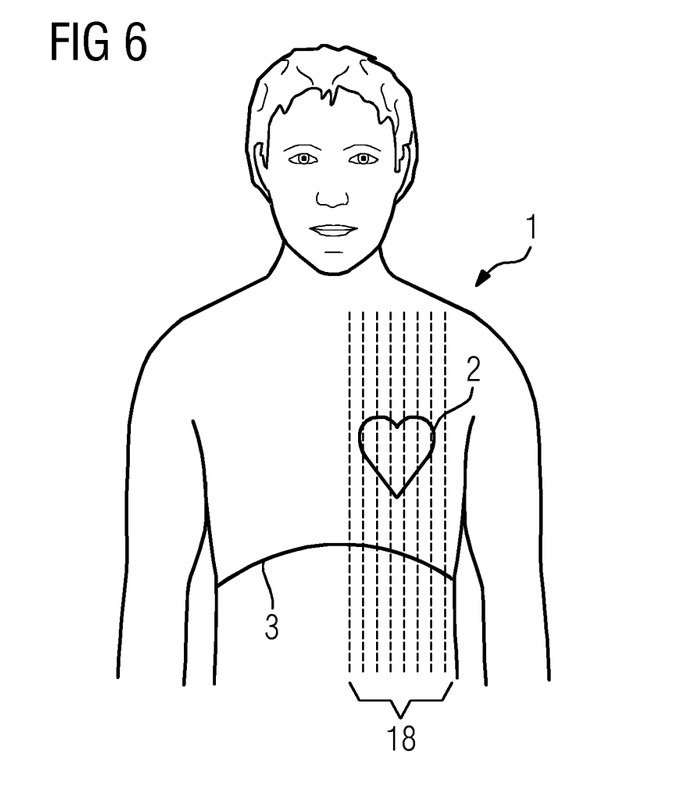
FIG. 6 shows a schematic representation of a fourth possible arrangement of the MR measurement regions for carrying out motion correction of the motion of a heart.

FIG. 6 shows a further possible arrangement of the MR measurement regions for identifying the motion of the heart. A plurality of two-dimensional MR measurements is used here. The two-dimensional measurement regions 18 run in parallel in the sagittal direction over the left half of the body of a person 1. The size of the two-dimensional measurement regions 18 is selected such that the body is completely mapped in the anterior-posterior direction and that in the longitudinal direction of the body at least the heart 2 and the diaphragm 3 are mapped. For greater clarity eight two-dimensional measurement regions 18 are mapped here. It may be advantageous to measure more than the eight measurement regions 18 shown in the left half of the body. Thus for example twenty measurement regions 18 can be measured, each of the layers of the measurement regions 18 being 8-10 mm thick and the individual measurement regions 18 having a spacing of 8-10 mm. In a measurement such as this a temporal resolution in the region of 10-20 ms can be achieved. Using several individual measurement regions 18 to determine the motion of heart 2 and diaphragm 3 has the advantage, compared to using a three-dimensional recording, that thanks to the spacing of the individual two-dimensional measurement regions 18 a faster measurement is possible, but the measurement data is not blurred over a wider region. The number of measurement regions 18 can of course be adjusted depending on the temporal and spatial resolution necessary.

Alternatively to the measurement shown in FIG. 6 using several parallel spaced regions 18, a similar measurement is also possible in which the individual two-dimensional regions are recorded in coronal orientation. Here too the measurement regions 18 should extend at least over the heart 2 and in part over the diaphragm 3. When using coronal parallel measurement regions particularly reliable measurements can be achieved, for example when using approx. 40 layers. In this case a temporal resolution of approx. 20-40 ms can be achieved.

Although the invention has been illustrated and described in detail on the basis of the preferred exemplary embodiment, the invention is not limited by the disclosed examples and other variations can be derived herefrom by the person skilled in the art, without departing from the scope of protection of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Although the invention has been illustrated and described in detail on the basis of the preferred example embodiment, the invention is not limited by the disclosed examples and other variations can be derived herefrom by the person skilled in the art, without departing from the scope of protection of the invention.

What is claimed is:

1. A method for motion correction of emission computed tomography data in a combination device for magnetic resonance tomography and emission computed tomography, the method comprising:
    recording emission computed tomography data over a recording period and storing associated detection events and detection instants;
    performing seperate magnetic resonance measurements for at least two subregions of an examination region of an examination object to record magnetic resonance data of the at least two subregions at at least two recording instants during the recording period of the emission computed tomography data;
    storing the recorded magnetic resonance data and the at least two recording instants;
    determining, for each of the at least two subregions, at least one item of motion information describing a motion of a region of the examination object at a first instant relative to a position at a second instant, from magnetic resonance data recorded at the first instant and the second instant;
    determining a motion model describing motion of the examination object, for the entire examination object, from the items of motion information for the at least two subregions; and
    calculating motion-corrected emission tomography data from the detection events, the detection instants and the motion model.

2. The method of claim 1, wherein the magnetic resonance data is recorded one- or two-dimensionally for at least one of the at least two subregions.

3. The method of claim 1, wherein the magnetic resonance data for at least one of the at least two subregions is recorded one-dimensionally using a two-dimensional high-frequency pulse.

4. The method of claim 1, wherein a time interval between two recordings of magnetic resonance data of a first of the at least two subregions differs from a time interval between two recordings of magnetic resonance data of at least a second of the at least two subregions.

5. The method of claim 1, wherein spatial resolutions of the seperate magnetic resonance measurements are different in at least two of the subregions.

6. The method of claim 1, wherein the seperate magnetic resonance measurements of at least two of the at least two subregions are performed at different instants.

7. The method of claim 1, further comprising: exiting at least two subvolumes for the seperate magnetic resonance measurements simultaneously.

8. The method of claim 7, wherein the exciting comprises:
    using at least two local coils to perform magnetic resonance measurements for the at least two subregions simultaneously, wherein
        coupling between the at least two subregions and the at least two local coils is based on respective distances between the at least two local coils and the at least two subregions.

9. The method of claim 7, wherein a simultaneous magnetic resonance measurement is performed for at least two of the at least two subregions by overlaying a second readout gradient.

10. The method of claim 1, wherein a time interval between two magnetic resonance measurements for at least one of the at least two subregions is between 1 and 100 ms.

11. The method of claim 1, wherein the emission computed tomography is PET.

12. The method of claim 1, wherein the calculating motion corrected emission tomography data corrects motion of a heart caused by a heartbeat.

13. A combined emission computed tomography and magnetic resonance tomography device, comprising:
    a control device configured to
        record emission computed tomography data over a recording period and storing associated detection events and detection instants,
        perform seperate magnetic resonance measurements for at least two subregions of an examination region of an object to record magnetic resonance data of at least two subregions at at least two recording instants during the recording period of the emission computed tomography data,
        store the recorded magnetic resonance data and the at least two recording instants,
        determine, for each of the at least two subregions, at least one item of motion information describing a motion of a region of the examination object at a first instance relative to a position at a second instant, from magnetic resonance data recorded at the first instant and the second instant.

determine a motion model describing motion of the examination object, for the entire examination object, from the items of motion information for the at least two subregions, and calculate motion-corrected emission tomography data from the detection events, the detection and the motion model.

14. The method of claim 10, wherein the time interval between two magnetic resonance measurements of the at least one of the at least two subregions is less than 40 ms.

15. A computer readable medium including program code segments for, when executed on a combined emission computed tomography and magnetic resonance tomography device, causing the combined emission computed tomography and magnetic resonance tomography device to perform a method comprising:

recording emission computed tomography data over a period and storing associated detection events and detection instants;

performing seperate magnetic resonance measurements for at least two subregions of an examination region of an examination object to record magnetic resonance data of at least two subregions at at least two recording instants during the recording period of the emission computed tomography data;

storing the recorded magnetic resonance data and the at least two recording instants;

determining, for each of the at least two subregions, at least one item of motion information describing a motion of a region of the examination object at a first instant relative to a position at a second instant, from magnetic resonance data recorded at the first instant and the second instant;

determining a motion model describing motion of the examination object, for the entire examination object, from the items of motion information for the at least two subregions; and calculating motion-corrected emission tomography data from the detection events, the detection instants and the motion model.

* * * * *